(12) United States Patent
Tsuchiya et al.

(10) Patent No.: US 10,980,914 B2
(45) Date of Patent: *Apr. 20, 2021

(54) ANTIBACTERIAL BIOLOGICAL IMPLANT

(71) Applicant: PROSTEC CO., LTD., Kanazawa (JP)

(72) Inventors: Hiroyuki Tsuchiya, Kanazawa (JP);
Yukinobu Hashimoto, Sabae (JP);
Mitsuyoshi Yamashita, Osaka (JP);
Keita Ishimizu, Osaka (JP); Natsumi Kageyama, Osaka (JP)

(73) Assignee: PROSTEC CO., LTD., Kanazawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/497,694

(22) PCT Filed: Mar. 31, 2017

(86) PCT No.: PCT/JP2017/013659
§ 371 (c)(1),
(2) Date: Sep. 25, 2019

(87) PCT Pub. No.: WO2018/179357
PCT Pub. Date: Oct. 4, 2018

(65) Prior Publication Data
US 2020/0023097 A1    Jan. 23, 2020

(51) Int. Cl.
*A61L 27/06* (2006.01)
*A61L 27/30* (2006.01)

(52) U.S. Cl.
CPC .......... *A61L 27/06* (2013.01); *A61L 27/30* (2013.01); *A61L 2300/106* (2013.01); *A61L 2420/02* (2013.01)

(58) Field of Classification Search
CPC .................................................. A61L 2300/106
See application file for complete search history.

(56) References Cited

U.S. PATENT DOCUMENTS

| | | | |
|---|---|---|---|
| 2009/0082865 A1* | 3/2009 | Raja | A61L 27/56 623/16.11 |
| 2011/0313539 A1 | 12/2011 | Tsuchiya et al. | |
| 2017/0007743 A1* | 1/2017 | Hedrick | C23C 22/78 |

FOREIGN PATENT DOCUMENTS

| | | |
|---|---|---|
| CN | 102416202 A | 4/2012 |
| EP | 2 371 398 A1 | 10/2011 |
| JP | 2932437 B1 | 8/1999 |
| JP | 5044795 B2 | 10/2012 |

OTHER PUBLICATIONS

Park et al. Effects of Anodizing Conditions on Bond Strength of Anodically Oxidized Film to Titanium Substrate. (Year: 2007).*

(Continued)

*Primary Examiner* — Sarah Alawadi
(74) *Attorney, Agent, or Firm* — Oblon, McClelland, Maier & Neustadt, L.L.P.

(57) ABSTRACT

Provided is an antibacterial biological implant capable of exhibiting superior antibacterial activity stably over a long period of time. The antibacterial biological implant 1 includes a substrate 2 made of a metal material and an anodized coating 3 provided on the substrate 2, the anodized coating 3 including an iodine-rich layer 31 located close to an interface S between the anodized coating 3 and the substrate 2.

12 Claims, 5 Drawing Sheets

(56) References Cited

OTHER PUBLICATIONS

Shirai et al. (Antibacterial Iodine-Supported Titanium Implants. (Year: 2010).*
International Search Report dated May 9, 2017 in PCT/JP2017/013659 filed on Mar. 31, 2017.
Tsuchiya, H. et al., "Innovative antimicrobial coating of titanium implants with iodine", Journal of Orthopedic Science, vol. 17, 2012, pp. 595-604.
Inaba, T. et al., "The Effects of Vacuum Heat Treatments on Bonding Strength of Anodically Oxidized Titanium and a Titanium Alloy", Journal of the Iron & Steel Institute of Japan (ISIJ), vol. 81, No. 6, 1995, pp. 84-89.
Kato, T., et al., "Temperal Attenuation of Iodine Content and its Effect on the Antibacterial Activity of Iodine-Supported Titanium Implants", Journal of Microbial & Biochemical Technology, vol. 8, No. 4, Jan. 1, 2016, pp. 285-289.

* cited by examiner

ANTIBACTERIAL BIOLOGICAL IMPLANT

TECHNICAL FIELD

The present invention relates to a biological implant having antibacterial activity.

BACKGROUND ART

Biological implants are intended to repair or replace part of a human body when the function of the part is reduced or lost by injury or disease. The number of people using biological implants is increasing with increasing elderly population. Such biological implants need to be capable of serving the biological function stably over a long period of time after surgery. The recent advancement of technology is marked also in the field of biological implants, and currently-available biological implants can exhibit a certain level of performance.

However, existing biological implants still have problems, an example of which is postoperative infection. After surgery for replacement with an implant such as an artificial joint, bacteria may proliferate around the implant or at the surgical site and cause an infection and, in the worst case, it is necessary to remove the infected artificial joint by second surgery, treat the infection with an antibiotic, and then place another artificial joint. In the event of a poor prognosis, the infection may cause an irreparable damage, leading, for example, to arthrodesis or amputation of a limb.

To address the above problem, investigations as to endowment of biological implants with antibacterial activity have been actively conducted in recent years. A known method for endowing a biological implant with antibacterial activity is one that uses iodine as an antibacterial substance. For example, in Patent Literatures 1 and 2, anodization or oxidation by a chemical treatment is performed to form microscopic holes or asperities, then the microscopic holes or asperities are impregnated with iodine or an iodine compound through electrophoresis, and the iodine is dissolved out to obtain antibacterial activity. It is desirable that such antibacterial activity attributed to iodine be stably exhibited over a long period of time.

CITATION LIST

Patent Literature

Patent Literature 1: Japanese Patent No. 2932437
Patent Literature 2: Japanese Patent No. 5044795

SUMMARY OF INVENTION

Technical Problem

An object of the present invention is to provide an antibacterial biological implant capable of exhibiting superior antibacterial activity stably over a long period of time.

Solution to Problem

As a result of intensive investigations aimed at solving the above problem, the present inventors have discovered a technical solution with the following features and completed the present invention.

(1) An antibacterial biological implant including: a substrate made of a metal material; and an anodized coating provided on the substrate, the anodized coating including an iodine-rich layer located close to an interface between the anodized coating and the substrate.

(2) The antibacterial biological implant according to (1), wherein the metal material is titanium or a titanium alloy.

(3) The antibacterial biological implant according to (1) or (2), wherein the iodine-rich layer is made of an inorganic compound containing at least iodine.

(4) The antibacterial biological implant according to any one of (1) to (3), wherein the iodine-rich layer is made of an inorganic compound containing at least iodine and an element derived from the substrate.

(5) The antibacterial biological implant according to any one of (1) to (4), wherein a portion of the anodized coating other than the iodine-rich layer is free of iodine.

(6) The antibacterial biological implant according to any one of (1) to (5), wherein the iodine-rich layer is in contact with the substrate.

(7) The antibacterial biological implant according to any one of (1) to (6), wherein an adhesive strength of the anodized coating to the substrate, as measured according to ASTM F1147, is 22 MPa or more.

(8) The antibacterial biological implant according to any one of (1) to (7), having an iodine content of 4 to 16 $\mu g/cm^2$.

(9) The antibacterial biological implant according to any one of (1) to (8), having an iodine content of 10 to 16 $\mu g/cm^2$.

(10) The antibacterial biological implant according to any one of (1) to (9), capable of sustained-release of iodine.

Advantageous Effects of Invention

The present invention provides the advantage of making it possible to obtain an antibacterial biological implant capable of exhibiting superior antibacterial activity stably over a long period of time.

BRIEF DESCRIPTION OF DRAWINGS

FIG. 3A shows a field emission scanning electron microscope photograph and FIG. 3B shows iodine element mapping (FIG. 1 is a schematic version of FIG. 3).

FIG. 4A shows a field emission scanning electron microscope photograph and FIG. 4B shows iodine element mapping.

DESCRIPTION OF EMBODIMENTS

<Antibacterial Biological Implant>

Hereinafter, an antibacterial biological implant (occasionally referred to as "biological implant" in the following description) according to an embodiment of the present invention will be described in detail with reference to FIG. 1.

Figure 1:
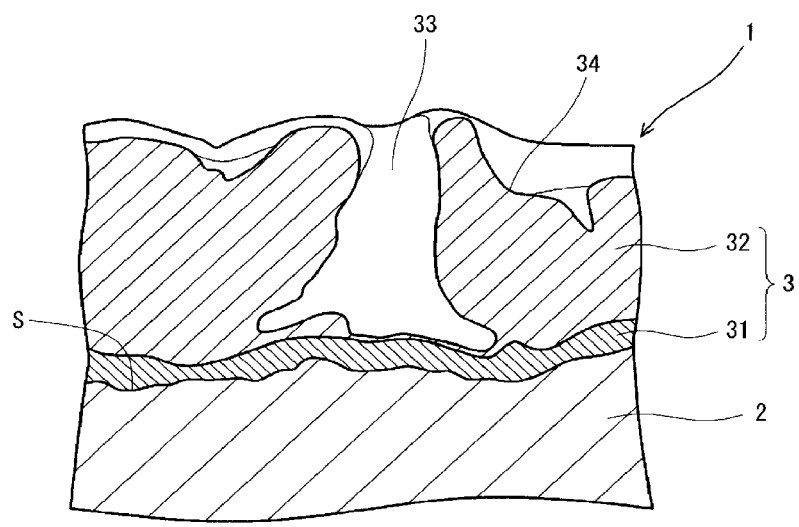
FIG. 1 is a partially enlarged schematic cross-section illustrating an antibacterial biological implant according to an embodiment of the present invention.

A biological implant 1 of the present embodiment is shown in FIG. 1. The biological implant 1 has antibacterial activity attributed to iodine and includes a substrate 2 and an anodized coating 3.

(Substrate)

The substrate 2 is made of a metal material. Examples of the metal material include titanium, cobalt, a titanium alloy, a cobalt alloy, a cobalt-chromium alloy, and stainless steel. The metal material is not limited to these examples and may be any metal material usable in biological implants.

Among the metal materials mentioned as examples, titanium or a titanium alloy is preferred because of their high affinity for bone, superior bond strength to bone, and high biocompatibility. That is, the metal material of the present embodiment is preferably titanium or a titanium alloy. Preferred examples of the titanium are those specified as Grades 1 to 4 in ASTM F67. Examples of the titanium alloy include Ti-6Al-4V ELI alloy (ASTM F136), Ti-6Al-7Nb alloy (ASTM F1295), Ti-6Al-2Nb-1Ta-0.8Mo alloy (JIS T 7401-3), and Ti-15Mo-5Zr-3Al alloy (ISO 5832-14). Among the examples of the titanium and titanium alloy, a titanium alloy consisting of Ti-6Al-4V ELI alloy (ASTM F136) is more preferred.

(Anodized Coating)

The anodized coating 3 is a coating provided on the substrate 2 described above, and is formed through an anodization treatment described later. Thus, the anodized coating 3 of the present embodiment has microscopic holes 33 and microscopic asperities 34 which are formed as a result of the anodization treatment. The microscopic hole 33 is a circular or polygonal hole having a circle-equivalent diameter, as calculated on an area basis, of 0.1 to 5 μm. The microscopic asperity 34 is an asperity formed as a result of deformation of the microscopic hole 33 or joining of the adjacent microscopic holes 33. The microscopic asperities 34 exhibit an arithmetic mean roughness (Ra), as measured according to JIS B 0601-2001, of 0.2 μm or more. Impregnating such microscopic holes 33 and microscopic asperities 34 with iodine or an iodine compound can achieve antibacterial activity. However, the iodine or iodine compound impregnating the microscopic holes 33 and microscopic asperities 34 readily dissolves out, and the antibacterial activity attributed to the iodine or iodine compound declines relatively quickly. This tendency is evident in a step of a method for producing the biological implant 1, in particular in a washing treatment following an iodine treatment described later.

The anodized coating 3 of the present embodiment includes an iodine-rich layer 31. The iodine-rich layer 31 is a layer portion that has the highest iodine content in the anodized coating 3. The term "iodine content" refers to the amount of iodine element as a constituent of iodine or an iodine compound. In the present embodiment, the iodine-rich layer 31 is located close to an interface S between the anodized coating 3 and the substrate 2. With this feature, iodine or an iodine compound in the iodine-rich layer 31 can be prevented from easily dissolving out of the iodine-rich layer 31, and sustained-release of iodine can be maintained over time. Even when the implant is subjected to a washing treatment after the iodine treatment, superior antibacterial activity attributed to iodine can be stably obtained over a long period of time.

The fact that the anodized coating 3 includes the iodine-rich layer 31 can be confirmed, for example, by subjecting the implant to cross-section polisher (hereinafter occasionally referred to as "CP") processing, then observing the resulting cross-section with a field emission scanning electron microscope (hereinafter occasionally referred to as "FE-SEM") and subjecting the cross-section to element mapping using an energy dispersive X-ray spectrometer (hereinafter occasionally referred to as "EDS").

In the present embodiment, the iodine-rich layer 31 is the portion of the anodized coating 3 that is closest to the interface S between the anodized coating 3 and the substrate 2. In other words, the iodine-rich layer 31 is located between a portion 32 of the anodized coating 3 other than the iodine-rich layer 31 and the substrate 2. Thus, in the present embodiment, the iodine-rich layer 31 is in contact with the substrate 2. With this feature, it is possible to prevent iodine from easily dissolving out. Stating that "the iodine-rich layer 31 is in contact with the substrate 2" means that the iodine-rich layer 31 is substantially in contact with the substrate 2. That is, the statement that "the iodine-rich layer 31 is in contact with the substrate 2" is intended to include the case where most of the iodine-rich layer 31 is in contact with the substrate 2 and the remaining small portion of the iodine-rich layer 31 is away from the substrate 2 and in proximity to the interface S between the anodized coating 3 and the substrate 2.

The iodine-rich layer 31 of the present embodiment is made of an inorganic compound containing at least iodine. More specifically, the iodine-rich layer 31 is made of an inorganic compound containing at least iodine and an element derived from the substrate 2. With this feature, it is possible to prevent iodine from easily dissolving out. The iodine-rich layer 31 of the present embodiment is made of an inorganic compound containing not only an element derived from the substrate 2 but also an element derived from a bath used in the iodine treatment described later.

In the anodized coating 3 of the present embodiment, the portion 32 other than the iodine-rich layer 31 is free of iodine. This makes it possible to release iodine or an iodine compound stably over a long period of time, thus achieving superior sustained-release performance. Stating that a portion is free of iodine means that when the implant is subjected to CP processing and then the resulting cross-section is observed with an FE-SEM and subjected to element mapping using an EDS, iodine is not detected in the portion of interest at a concentration exceeding a level attributable to measurement error and inevitable impurities. The statement that a portion is free of iodine is not intended to exclude the case where iodine is detected due to measurement error or inevitable impurities as in the case with the portion 32 of FIG. 3B. The portion 32 of the present embodiment is made of an inorganic compound containing an element derived from the substrate 2 and an element derived from a bath used in the anodization treatment.

The thickness of the anodized coating 3 is preferably 3 to 10 μm. As for the upper limit, the thickness may be 6 μm or less or may be 5 μm or less. When the thickness is 3 μm or more, a sufficient amount of iodine or iodine compound can be included in the iodine-rich layer 31, and superior antibacterial activity can be stably exhibited over a longer period of time. If the thickness exceeds 10 μm, the adhesive strength of the anodized coating may decrease.

The thickness of the iodine-rich layer 31 is preferably 0.1 to 2 μm. In this case, a sufficient amount of iodine or iodine compound can be included in the iodine-rich layer 31, and superior antibacterial activity can be stably exhibited over a longer period of time.

The thickness of the anodized coating 3 and the thickness of the iodine-rich layer 31 can be measured by subjecting the implant to CP processing and then observing the resulting cross-section with an FE-SEM. The thickness is measured at five sites for each of the anodized coating 3 and the iodine-rich layer 31, and the average of the five values is determined as the thickness of the anodized coating 3 or the iodine-rich layer 31. When the thickness of the iodine-rich layer 31 is measured, element mapping using an EDS may be performed to identify the iodine-rich layer 31.

The adhesive strength of the anodized coating 3 to the substrate 2 is preferably 22 MPa or more. In this case, superior bond strength to bone can be achieved, and the requirement that the adhesive strength (static tensile strength) between a coating and a substrate in a medical component should be 22 MPa or more can be met. The upper limit of the adhesive strength, which depends on the strength of the adhesive agent used, may be about 70 MPa. The adhesive strength is determined by measurement according to ASTM F1147.

As for the upper limit of the iodine content of the biological implant 1, the iodine content may be 25 μg/cm$^2$ or less, 20 μg/cm$^2$ or less, or 16 μg/cm$^2$ or less. As for the lower limit, the iodine content may be 4 μg/cm$^2$ or more or 8 μg/cm$^2$ or more. The iodine content may be 4 to 20 μg/cm$^2$ or 4 to 16 μg/cm$^2$, and is preferably 10 to 16 μg/cm$^2$. With this feature, a sufficient iodine content for allowing the antibacterial activity to be exhibited over a long period of time can be ensured while the above-described adhesive strength of the anodized coating 3 to the substrate 2 is maintained. The iodine content is determined by measurement using an energy dispersive X-ray spectrometer. The iodine content in the present embodiment is measured after the washing treatment following the iodine treatment.

Examples of the form of the biological implant 1 described above include, but are not limited to, an artificial joint, an artificial bone, an artificial tooth root, an internal-external fixation material, and an external fixator.

<Method for Producing Antibacterial Biological Implant>

Next, a method for producing an antibacterial biological implant according to an embodiment of the present invention will be described in detail with reference to FIG. 2 by using an example where the biological implant 1 described above is produced.

Figure 2:
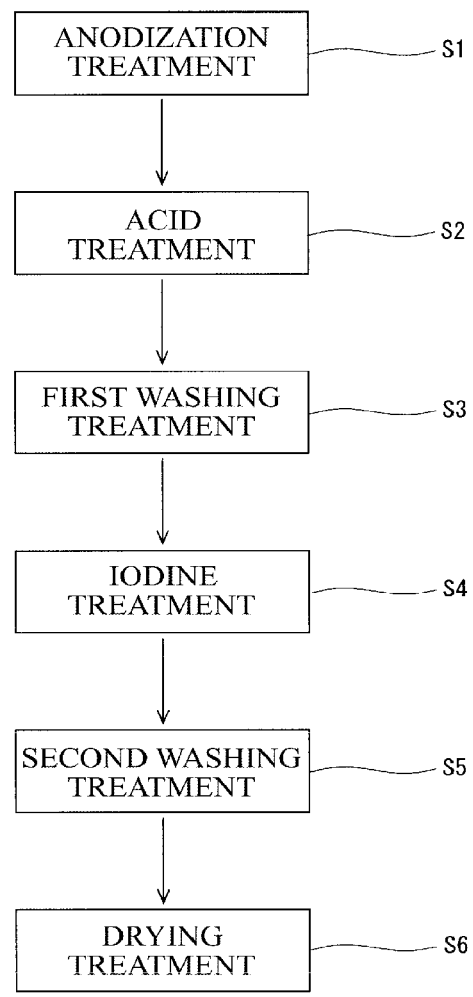
FIG. 2 is a flowchart illustrating a method for producing an antibacterial biological implant according to an embodiment of the present invention.

In the present embodiment, as shown in FIG. 2, the substrate 2 described above is subjected successively to an anodization treatment of step S1, an acid treatment of step S2, and an iodine treatment of step S4, and thus the biological implant 1 is obtained. In the present embodiment, the iodine treatment of step S4 is followed by a second washing treatment of step S5. In the present embodiment, a first washing treatment of step S3 and a drying treatment of step S6 are also performed. The anodization treatment of step S1 may be preceded by a degreasing treatment of step S0. Hereinafter, steps S0 to S6 of the present embodiment will be sequentially described in detail.

(Step S0: Degreasing Treatment)

The degreasing treatment is a treatment in which impurities such as dirt are removed from the surface of the substrate 2. For example, ultrasonic washing or immersion washing may be employed. Examples of the washing liquid used include an aqueous solution containing sodium hydroxide and a surfactant. To remove the adhering washing liquid, the substrate 2 may be washed with running pure water.

(Step S1: Anodization Treatment)

The anodization treatment is a treatment in which the substrate 2 is immersed in an electrolyte solution and electrolysis is allowed to take place with the substrate 2 serving as an anode. This treatment can result in formation of an anodized coating having no iodine-rich layer 31 on the substrate 2.

Examples of the electrolyte solution include acidic electrolyte solutions containing sulfuric acid, such as a sulfuric acid-water mixed bath, a sulfuric acid-phosphoric acid-water mixed bath, a sulfuric acid-phosphoric acid-hydrogen peroxide-water mixed bath, and a sulfuric acid-phosphoric acid-ascorbic acid-water mixed bath. In each of the mixed baths mentioned as examples, the concentration of each of the components such as sulfuric acid can be chosen as appropriate. For example, in the case of the sulfuric acid-phosphoric acid-hydrogen peroxide-water mixed bath, the concentration of sulfuric acid may be 30 to 40 g/l, the concentration of phosphoric acid may be 20 to 30 g/l, and the concentration of hydrogen peroxide may be 5 to 15 g/l.

An alkaline electrolyte solution may be used instead of the acidic electrolyte solution as described above. Examples of the alkaline electrolyte solution include a potassium hydroxide-potassium fluoride-sodium phosphate-aluminum hydroxide-water mixed bath. As for the concentrations of the components in this mixed bath, for example, the concentration of potassium hydroxide may be 165 g/l, the concentration of potassium fluoride may be 35 g/l, the concentration of sodium phosphate may be 35 g/l, and the concentration of aluminum hydroxide may be 35 g/l.

When the substrate is made of titanium, a titanium alloy, or stainless steel, the use of an acidic electrolyte solution is preferred. When the substrate is made of a cobalt-chromium alloy, the use of an alkaline electrolyte solution is preferred.

The temperature of the electrolyte solution is preferably in the range of 23 to 40° C. and more preferably in the range of 23 to 35° C. As described later, main electrolysis involves spark discharge leading to generation of Joule heat which would cause temperature increase. Excessive temperature increase can cause separation of the anodized coating. Thus, during the reaction, it is preferable to keep the temperature of the electrolyte solution within the above range, for example, by cooling the electrolyte solution or avoiding a sharp increase in voltage.

The current used for the electrolysis is a pulsating direct current. The frequency of the pulsating direct current is preferably 50 Hz or more. This is because a significant increase in antibacterial activity can be achieved as compared to the case of an anodization treatment with application of a mere direct current. As for the lower limit of the frequency, the frequency is preferably 50 Hz or more, more preferably 200 Hz or more, even more preferably 800 Hz or more, and still even more preferably 1000 Hz or more and, as for the upper limit, the frequency is preferably 10,000 Hz or less and more preferably 5000 Hz or less. This is because the antibacterial activity is significantly increased.

The electrolysis preferably includes preliminary electrolysis and main electrolysis. As for the conditions of the preliminary electrolysis, the voltage used is equal to or lower than the maximum voltage in a voltage range over which spark discharge (plasma discharge) does not occur. In the preliminary electrolysis, it is preferable to increase the voltage gradually from 0 Vrms to a predetermined voltage. The voltage application time employed in the preliminary electrolysis is preferably 10 seconds to 2 minutes, more preferably 20 seconds to 1 minute, even more preferably 30 seconds to 1 minute, from the moment when the predetermined voltage is reached.

The voltage employed in the main electrolysis is preferably 100 to 210 Vrms, more preferably 140 to 210 Vrms, and even more preferably 170 to 210 Vrms. The use of such a voltage can cause spark discharge. If the voltage is too low, spark discharge (plasma discharge) may not occur, and the microscopic holes 33 and microscopic asperities 34 may not be formed. If the voltage is too high, separation of the coating may occur.

The voltage application time employed in the main electrolysis is preferably 3 to 10 minutes, more preferably 5 to 10 minutes, and even more preferably 6 to 10 minutes. If the application time is too short, the thickness of the coating will be insufficient, while if the time is too long, separation of the coating will occur.

For example, as for the conditions of the preliminary electrolysis and main electrolysis in the case where titanium or a titanium alloy is used as the material of the substrate, the preliminary electrolysis may use a pulsating direct-current voltage and consist of increasing the voltage from 0 Vrms to a predetermined voltage equal to or lower than 120 Vrms and then allowing the electrolysis process to proceed at the predetermined voltage for 10 seconds to 2 minutes, while the main electrolysis may use a pulsating direct-current voltage and consist of allowing the electrolysis process to proceed at a voltage of 120 to 210 Vrms for 3 to 10 minutes.

(Step S2: Acid Treatment)

The acid treatment is a treatment in which the substrate 2 and the anodized coating having no iodine-rich layer 31 are immersed in an acid. Through this treatment, part of a barrier layer which is located at the bottom of the microscopic hole 33 formed above the surface of the substrate and which is in contact with the substrate can be damaged to allow sufficient electrolysis to occur in the iodine treatment described later. This can result in formation of the iodine-rich layer 31 and an increase in iodine content.

A possible reason for this effect is as follows. For example, when the anodization treatment described above is performed using a sulfuric acid-phosphoric acid-hydrogen peroxide-water mixed bath as the electrolyte solution and using a titanium alloy specified in ASTM F136 as the metal material of the substrate 2, the anodized coating has a sulfur-rich layer formed at and in the vicinity of the interface S between the anodized coating and the substrate 2. The sulfur-rich layer is made of an inorganic compound containing at least sulfur and is a layer portion having the highest sulfur content in the anodized coating. With the above combination of the electrolyte solution and the metal material, the sulfur-rich layer is made of an inorganic compound containing sulfur and titanium which is an element derived from the substrate 2 and further containing oxygen. When the anodized coating having such a sulfur-rich layer is subjected to the acid treatment together with the substrate 2, the sulfur-rich layer or part of the sulfur-rich layer is dissolved by the acid. It is presumed that the iodine treatment described later results in formation of an iodine-rich layer in the region from which the sulfur-rich layer has been dissolved away and therefore formation of the iodine-rich layer 31 located close to the interface S between the anodized coating and the substrate 2. With the above combination of the electrolyte solution and the metal material, a portion of the anodized coating other than the sulfur-rich layer is made of an inorganic compound containing titanium, aluminum, oxygen, and phosphorus.

Examples of the acid used in the acid treatment include sulfuric acid, hydrochloric acid, nitric acid, and oxalic acid. The acids mentioned as examples may be used alone, or a mixture of two or more of the acids may be used. Among the acids mentioned as examples, sulfuric acid is preferred. In other words, the acid treatment is preferably a treatment with sulfuric acid. It is preferable to use the acid(s) as mentioned above in combination with hydrogen peroxide.

The acid is preferably used in the form of an aqueous solution. The concentration of the acid in the aqueous solution is preferably 5 to 20 mass % and more preferably 5 to 15 mass %.

The temperature of the aqueous acid solution is preferably 40 to 70° C. and more preferably 50 to 70° C. If the temperature of the solution is extremely low, the formation of the iodine-rich layer 31 tends to fail. If the temperature of the solution is extremely high, the adhesive strength of the anodized coating 3 to the substrate 2 may decrease.

The immersion time is preferably 1 to 10 minutes and more preferably 1 to 5 minutes. If the immersion time is extremely short, the formation of the iodine-rich layer 31 tends to fail. If the immersion time is extremely long, the adhesive strength of the anodized coating 3 to the substrate 2 may decrease.

It is preferable to adjust the conditions of the acid treatment as appropriate depending on the type of the metal material of the substrate. For example, when the metal material is pure titanium, the aqueous acid solution may be formulated as an aqueous solution of 10 mass % sulfuric acid and 10 mass % hydrogen peroxide, and the immersion time may be set to 7 minutes. When the metal material is Ti-6Al-4V ELI alloy (ASTM F136), the aqueous acid solution may be formulated as an aqueous solution of 10 mass % sulfuric acid, and the immersion time may be set to 3 minutes. When the metal material is Ti-6Al-7Nb alloy (ASTM F1295), the aqueous acid solution may be formulated as an aqueous solution of 10 mass % sulfuric acid and 10 mass % hydrogen peroxide, and the immersion time may be set to 10 minutes.

(Step S3: First Washing Treatment)

The first washing treatment is a treatment performed after the above-described acid treatment to wash away the acid adhering to the substrate 2 and anodized coating having no iodine-rich layer 31. The washing liquid is, for example, but not limited to, pure water. The temperature of the washing liquid is preferably 20 to 30° C. Examples of the washing method include, but are not limited to, rinsing and immersion washing.

(Step S4: Iodine Treatment)

The iodine treatment is a treatment in which the substrate 2 and the anodized coating having no iodine-rich layer 31 are immersed in an electrolyte solution containing iodine or an iodine compound and electrolysis is allowed to take place with the substrate 2 serving as an anode. This treatment can result in the formation of the iodine-rich layer 31 located close to the interface S between the anodized coating 3 and the substrate 2, thus producing the biological implant 1. When the above-described anodization treatment is performed using a sulfuric acid-phosphoric acid-hydrogen peroxide-water mixed bath as the electrolyte solution and using a titanium alloy specified in ASTM F136 as the metal material of the substrate 2, the iodine-rich layer 31 is made of an inorganic compound containing iodine and titanium which is an element derived from the substrate 2 and further containing oxygen. With the above combination of the electrolyte solution and the metal material, the portion 32 of the anodized coating 3 other than the iodine-rich layer 31 is made of an inorganic compound containing titanium, aluminum, oxygen, and phosphorus.

Examples of the iodine compound used in the iodine treatment include an inorganic iodine compound and an organic iodine compound. Examples of the inorganic iodine compound include silver iodide, potassium iodide, nickel iodide, iron iodide, and tin iodide. Examples of the organic iodine compound include: chain saturated hydrocarbons such as methyl iodide, ethyl iodide, propyl iodide, butyl iodide, and isopropyl iodide; derivatives of such chain saturated hydrocarbons; chain unsaturated hydrocarbons such as vinyl iodide, allyl iodide, crotyl iodide, propargyl iodide, and iodophenylacetylene; derivatives of such chain unsaturated hydrocarbons; aromatic hydrocarbons such as iodobenzene, benzyl iodide, benzoyl iodide, phenacyl iodide, xylylene iodide, iodophthalein, iodohydroquinone, and cyclodextrin-iodine inclusion complex; derivatives of such aromatic hydrocarbons; hetero compounds such as trimethylsulfonium iodide and triphenylsulfonium iodide; and hetero compound polymers such as polyvinylpyrrolidone iodine (hereinafter occasionally referred to as "PVPI") and polyvinylphthalimide iodine. The iodine compounds mentioned as examples may be used alone, or a mixture of two or more of the iodine compounds may be used.

Among the iodine compounds mentioned as examples, PVPI is preferred in terms of safety for use in human bodies, environmental preservation, and biocompatibility.

The iodine and iodine compound are preferably used in the form of aqueous solutions. The concentration of the iodine or iodine compound in the aqueous solution is preferably 0.1 to 10.0 mass % and more preferably 0.4 to 6.0 mass %.

The temperature of the aqueous solution of the iodine and/or iodine compound is preferably 20 to 40° C., more preferably 23 to 40° C., and even more preferably 23 to 35° C.

The current used in the electrolysis is a direct current. The current density is preferably kept constant and more preferably kept constant in the range of 0.05 to 10 A/dm$^2$.

The voltage used in the electrolysis is preferably 100 to 250 Vrms and more preferably 100 to 200 Vrms. The electrolysis time is preferably 1 to 20 minutes and more preferably 3 to 18 minutes.

The electrolysis is preferably performed in two stages. The first-stage electrolysis is preferably allowed to proceed at a constant voltage equal to or lower than the voltage used in the second-stage electrolysis. The voltage used in the first-stage electrolysis is preferably 0 to 150 Vrms. The voltage used in the second-stage electrolysis is preferably 100 to 250 Vrms, more preferably 150 to 250 Vrms, and even more preferably 180 to 210 Vrms. For example, when titanium or a titanium alloy is used as the material of the substrate, the first-stage electrolysis is performed in which electrolysis is allowed to proceed, for example, at voltages ranging from 0 to about 120 or 150 Vrms for a given period of time, and then the second-stage electrolysis is performed in which electrolysis is allowed to proceed at a voltage of about 150 Vrms to 250 Vrms.

The electrolysis time (the total time of the first-stage electrolysis and the second-stage electrolysis when the electrolysis is performed in two stages) is preferably 1 to 20 minutes and more preferably 3 to 18 minutes. In particular, increasing the time of the second-stage electrolysis can lead to an increased iodine content.

By adjusting the iodine treatment conditions illustrated above, the iodine content previously described can be controlled to a desired level. It is preferable to adjust the conditions of the acid treatment as appropriate depending on the type of the metal material of the substrate. For example, when the metal material is pure titanium, the first-stage electrolysis may be performed at voltages ranging from 0 to 150 Vrms for 8 minutes, and the second-stage electrolysis may be performed at a voltage of 210 Vrms for 7 minutes. When the metal material is Ti-6Al-4V ELI alloy (ASTM F136), the first-stage electrolysis may be performed at voltages ranging from 0 to 150 Vrms for 6 minutes, and the second-stage electrolysis may be performed at a voltage of 180 Vrms for 7 minutes. When the metal material is Ti-6Al-7Nb alloy (ASTM F1295), the first-stage electrolysis may be performed at voltages ranging from 0 to 150 Vrms for 6 minutes, and the second-stage electrolysis may be performed at a voltage of 210 Vrms for 7 minutes.

(Step S5: Second Washing Treatment)

The second washing treatment is a treatment in which excess iodine or iodine compound adhering to the biological implant 1 is washed away. With this treatment, a packaging material in which the biological implant 1 is packaged can be prevented from being discolored or degraded due to the iodine or iodine compound adhering to the packaging material, and thus the biological implant 1 can be stored stably. Additionally, since the anodized coating 3 includes the iodine-rich layer 31, the biological implant 1 can maintain a sufficient iodine content even after the second washing treatment and can therefore exhibit superior antibacterial activity stably over a long period of time.

The washing liquid is, for example, but not limited to, pure water. The temperature of the washing liquid is preferably 40 to 60° C. With this temperature, excess iodine or iodine compound adhering to the biological implant 1 can be fully washed away. The washing method is preferably immersion washing. The immersion time is preferably 1 to 10 minutes and more preferably 3 to 7 minutes. When pure water is used as the washing liquid and the temperature of the liquid is set to the temperature as mentioned above, the second washing treatment is what may be called "hot water washing".

(Step S6: Drying Treatment)

The drying treatment is a treatment in which the biological implant 1 subjected to the second washing treatment is dried. The drying temperature is preferably 20 to 70° C. The drying time is preferably 1 to 15 minutes. The drying treatment is not limited to the drying conditions as mentioned above and may be performed under any conditions as long as the biological implant 1 can be dried.

EXAMPLES

Hereinafter, the present invention will be described in detail with examples. However, the present invention is not limited to the examples presented below. In the examples presented below, the anodization treatment, the acid treatment, and the iodine treatment were performed as follows.

(Anodization Treatment)

Two-stage electrolysis consisting of preliminary electrolysis (at the maximum voltage in a voltage range over which spark discharge does not occur) and main electrolysis was performed in an acidic electrolyte solution (solution temperature: 30° C.) prepared as a sulfuric acid (35 g/l)-phosphoric acid (25 g/l)-hydrogen peroxide (5 g/l)-water mixed bath. The preliminary electrolysis was performed using a pulsating direct-current voltage ranging from 0 to 120 Vrms for 2 minutes (in particular, the electrolysis was performed in the voltage range from 0 to 120 Vrms for 90 seconds and then at 120 Vrms for 30 seconds). Subsequently, the main electrolysis was performed in which electrolysis was allowed to proceed at a constant voltage of 150 Vrms or 175 Vrms for 5 minutes or 8 minutes.

(Acid Treatment)

The acid treatment was performed by immersion in a 10 mass % aqueous sulfuric acid solution (solution temperature: 55° C.) for 3 minutes.

(Iodine Treatment)

Electrolysis was allowed to take place in a 0.5 mass %, 3.5 mass %, or 5.0 mass % aqueous PVPI solution (solution temperature: 25° C.). The electrolysis process was performed at a constant voltage of 120 Vrms or 150 Vrms for 5 minutes or 15 minutes, with the initial current density set to 1 to 2 A/dm$^2$.

Examples 1 to 4

<Preparation of Biological Implant>

A machined titanium alloy made from Ti-6Al-4V ELI (size: 5 cm×5 cm, thickness: about 1 mm) was prepared as a substrate and this substrate was used as a test specimen, which was subjected successively to the degreasing treatment, the anodization treatment, the acid treatment, the first washing treatment, the iodine treatment, the second washing treatment, and the drying treatment. Specifically, first, the test specimen was subjected to the degreasing treatment, in which the test specimen was alkali-treated under sonication at 45° C. using 10% Dyclen EW (manufactured by MacDermid Performance Solutions Japan K.K.) as a washing liquid and then washed with running pure water. Next, the anodization treatment was performed under the conditions shown in Table 1 (the voltage and time listed in the column headed "Anodization treatment" of Table 1 are those used in the main electrolysis), and subsequently the acid treatment was performed. Further, the test specimen was subjected to the first washing treatment, in which the test specimen was thoroughly rinsed with pure water (water temperature: 23° C., i.e., room temperature) and after which the iodine treatment was performed under the conditions shown in Table 1. Subsequently, the test specimen was subjected to the second washing treatment to wash away excess iodine compound adhering to the test specimen, and then subjected to the drying treatment, as a result of which a biological implant having an anodized coating provided on the substrate was obtained. The second washing treatment was performed as hot water washing in which the test specimen was immersed in pure water (water temperature: 45° C.) for 5 minutes. In the drying treatment, the drying temperature was 60 to 70° C., and the drying time was 10 minutes.

<Evaluation>

The biological implants thus obtained were each evaluated for the iodine content and the adhesive strength of the anodized coating to the substrate. The evaluation methods are described below, and the evaluation results are shown in Table 1.

(Iodine Content)

The amount of iodine remaining after the hot water washing was measured using EDX-GP, an energy dispersive X-ray spectrometer manufactured by Shimadzu Corporation. The analysis conditions were as follows.

Accelerating voltage: 50 keV

Measurement time: 100 seconds

Other conditions: A KI standard sample was used to set a sensitivity coefficient, and then the iodine content was evaluated.

(Adhesive Strength)

The adhesive strength of the anodized coating to the substrate was measured according to ASTM F1147. The results are shown in the column headed "Adhesive strength" of Table 1. The details of the measurement conditions were as follows.

Apparatus: 55R1123, manufactured by Instron

Crosshead speed: 2.5 mm/min

Adhesive agent: FM1000, a polyamide-epoxy resin-based adhesive sheet manufactured by Cytec Engineered Materials Inc.

Comparative Example 1 and Comparative Example 2

Biological implants were obtained in the same manner as in Examples 1 to 4 described above, except that the test specimen was not subjected to the acid treatment. Specifically, first, a machined titanium alloy made from Ti-6Al-4V ELI was prepared as a substrate and this substrate was used as a test specimen, which was subjected to the degreasing treatment and to the anodization treatment under the conditions shown in Table 1. Next, the test specimen was subjected to the first washing treatment in the same manner as in Examples 1 to 4 described above, and then subjected to the iodine treatment under the conditions shown in Table 1. The test specimen was subjected successively to the second washing treatment and the drying treatment in the same manner as in Examples 1 to 4 described above to obtain a biological implant having an anodized coating provided on the substrate. The biological implants thus obtained were each evaluated for the iodine content and the adhesive strength of the anodized coating in the same manner as in Examples 1 to 4 described above.

TABLE 1

| | Anodization treatment | | | Iodine treatment | | | | |
| --- | --- | --- | --- | --- | --- | --- | --- | --- |
| | | | | Concentration of aqueous PVPI | | | | |
| | Voltage (V) | Time (minutes) | Acid treatment | solution (mass %) | Voltage (V) | Time (minutes) | Iodine content (μg/cm$^2$) | Adhesive strength (MPa) |
| Example 1 | 175 | 8 | Performed | 3.5 | 120 | 5 | 4.6 | 61 |
| Example 2 | 175 | 8 | Performed | 5.0 | 150 | 5 | 10.3 | 37 |
| Example 3 | 175 | 8 | Performed | 5.0 | 150 | 15 | 15.4 | 23 |
| Example 4 | 175 | 8 | Performed | 0.5 | 150 | 5 | 8.3 | 53 |
| Comparative Example 1 | 150 | 5 | Not performed | 0.5 | 120 | 5 | 2.1 | 60 |
| Comparative Example 2 | 175 | 8 | Not performed | 0.5 | 150 | 5 | 2.5 | 58 |

As clearly seen from Table 1, the iodine content was higher in all of Examples 1 to 4 than in Comparative Examples 1 and 2. It is also seen that changing the conditions of the iodine treatment causes a change in the iodine content. It is also seen that the adhesive strength decreases with increasing iodine content. It is also seen that when the iodine content is in the range of 4 to 16 µg/cm$^2$, the requirement that the adhesive strength of a coating to a substrate in a medical component should be 22 MPa or more can be fulfilled.

Figure 3A:
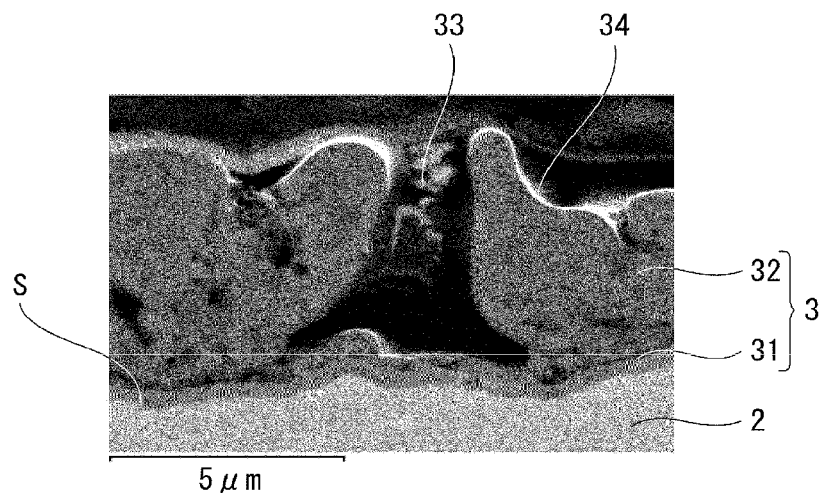
FIGS. 3A and 3B show the results of cross-sectional observation in Example 2, where
Figure 3B:
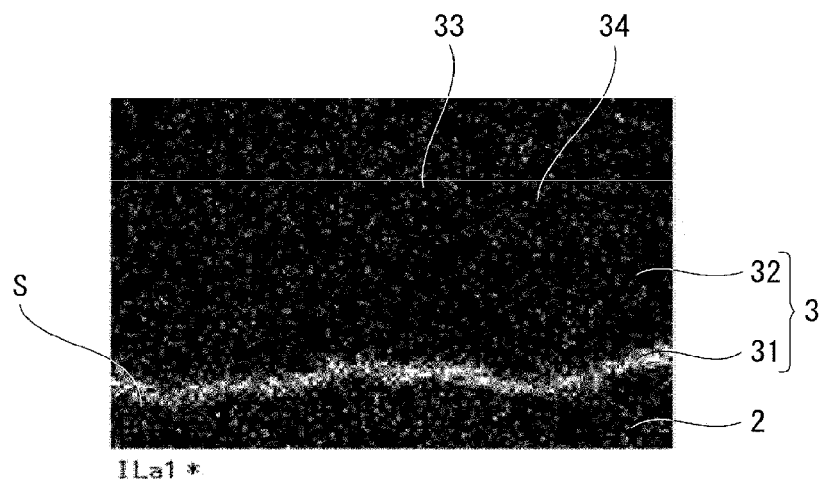
Figure 4A:
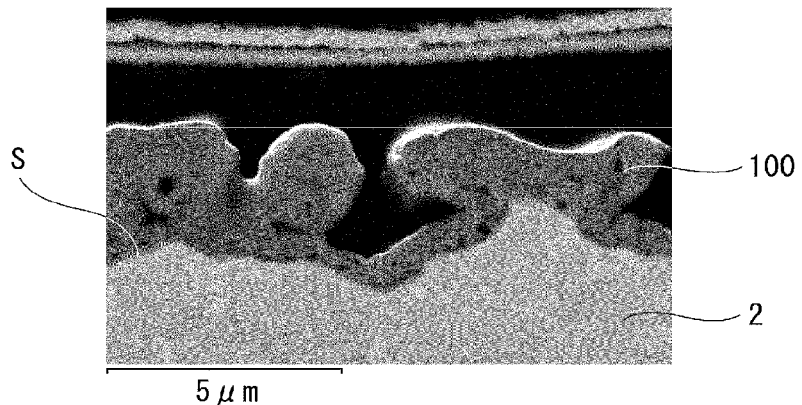
FIGS. 4A and 4B show the results of cross-sectional observation in Comparative Example 1, where
Figure 4B:
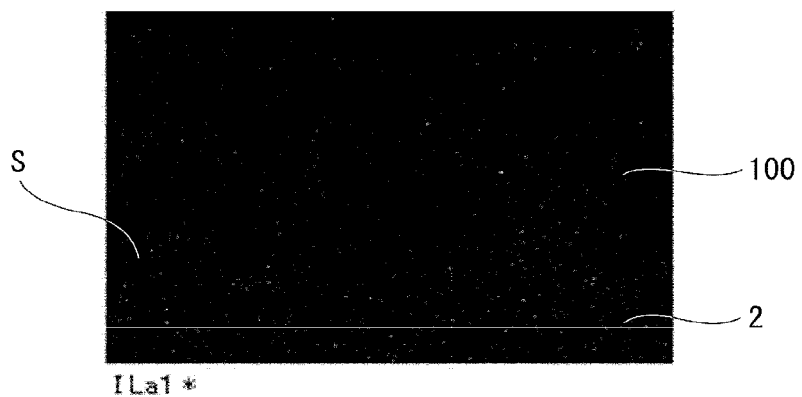

Each of the biological implants of Example 2 and Comparative Example 1 described above was further subjected to CP processing, after which the resulting cross-section was observed with an FE-SEM and subjected to element mapping using an EDS. The conditions of the procedures are listed below. The results of the cross-sectional observation in Example 2 are shown in FIG. 3A and FIG. 3B, which respectively show a field emission scanning electron microscope photograph and element mapping. The results of the cross-sectional observation in Comparative Example 1 are shown in FIG. 4A and FIG. 4B, which respectively show a field emission scanning electron microscope photograph and element mapping.

(Conditions of CP Processing)
Apparatus: SM-09010, manufactured by JEOL Ltd.
Accelerating voltage: 6.0 kV
Processing time: 3.0 hours
Processing range: From surface to a depth of 25 µm
(Conditions of FE-SEM Observation)
Apparatus: JSM-7600F, manufactured by JEOL Ltd.
Accelerating voltage: 5.0 kV
Detector: COMPO image
Observation magnification: 10,000 times
(Conditions of EDS Analysis)
Apparatus: X-act, manufactured by Oxford Instruments plc
Accelerating voltage: 10 kV
Mapping target elements: Carbon, titanium, oxygen, vanadium, aluminum, phosphorus, and iodine In the biological implant of Example 2, as is clear from FIGS. 3A and 3B, iodine was not present in the microscopic holes 33 and microscopic asperities 34 formed by the anodization treatment. This is presumably because iodine was washed away from the microscopic holes 33 and microscopic asperities 34 by the hot water washing following the iodine treatment.

In the biological implant of Example 2, the anodized coating 3 included the iodine-rich layer 31 located close to the interface S between the anodized coating 3 and the substrate 2. The constituent elements of the portion 32 of the anodized coating 3 other than the iodine-rich layer 3 and the constituent elements of the iodine-rich layer 31 were identified using an EDS. As a result, the portion 32 was found to be constituted of titanium, aluminum, oxygen, and phosphorus. In other words, the portion 32 was made of an inorganic compound containing no iodine and containing titanium, aluminum, oxygen, and phosphorus. The iodine-rich layer 31 was constituted of iodine, titanium, and oxygen. In other words, the iodine-rich layer 31 was made of an inorganic compound containing iodine, titanium, and oxygen. Among these constituent elements, titanium and aluminum are thought to be components derived from Ti-6Al-4V of the substrate, and phosphorus, oxygen, and iodine are thought to be components derived from the baths used in the anodization treatment and iodine treatment.

As with the biological implant of Example 2, the biological implants of Examples 1, 3, and 4 were each subjected to CP processing, after which the resulting cross-section was observed with an FE-SEM and subjected to element mapping using an EDS. As a result, it was confirmed that in the biological implants of Examples 1, 3, and 4, the anodized coating 3 included the iodine-rich layer 31 located close to the interface S between the anodized coating 3 and the substrate 2, as in the biological implant of Example 2. In all of Examples 1 to 4, the iodine-rich layer 31 was located between the portion 32 of the anodized coating 3 other than the iodine-rich layer 31 and the substrate 2, and was in contact with the substrate 2.

For the biological implants of Examples 1 to 4, the thickness of the anodized coating 3 and the thickness of the iodine-rich layer 31 were measured. The measurement was performed at 10 sites by cross-sectional observation with an FE-SEM, and the averages were calculated. The results are shown in Table 2.

In the biological implant of Comparative Example 1, as is clear from FIGS. 4A and 4B, the anodized coating 100 did not have the iodine-rich layer 31. For the biological implant of Comparative Example 1, iodine was not detected. This result agrees with the above result that the iodine content was low in Comparative Example 1.

As with the biological implant of Comparative Example 1, the biological implant of Comparative Example 2 was also subjected to CP processing, after which the resulting cross-section was observed with an FE-SEM and subjected to element mapping using an EDS. As a result, it was found that in the biological implant of Comparative Example 2, the anodized coating 100 had no iodine-rich layer as in the biological implant of Comparative Example 1. Further, iodine was not detected for the biological implant of Comparative Example 2.

For the biological implants of Comparative Examples 1 and 2, the thickness of the anodized coating 100 was measured in the same manner as for the biological implants of Examples 1 to 4 described above. The results are shown in Table 2.

TABLE 2

|  | Thickness of anodized coating (µm) | Thickness of iodine-rich layer (µm) |
|---|---|---|
| Example 1 | 4.20 | 0.34 |
| Example 2 | 4.90 | 0.34 |
| Example 3 | 4.54 | 0.56 |
| Comparative Example 1 | 2.32 | — |

The biological implant of Example 2 described above was further subjected to an antibacterial test using a film attachment method according to JIS Z 2801. Specifically, a test specimen was formed to have a length of 50 mm, a width of 50 mm, and a thickness of 3 mm, and *Staphylococcus aureus* was used as bacteria in a bacterial suspension. A polyethylene film was used as a blank sample, and a polished surface prepared by polishing non-surface-treated Ti-6Al-4V ELI with SiC abrasive paper #120 was used as Comparative Example 3. The polyethylene film and the polished surface were also subjected to the antibacterial test in the same manner as the biological implant of Example 2. Table 3 shows the number of bacteria and the antibacterial activity level as measured after 24 hours. The values of the antibacterial activity level shown in Table 3 are each a difference in logarithmic value from the number of bacteria as measured for the blank sample after 24 hours. When the antibacterial activity level is 2 or higher, the implant can be determined to have the antibacterial activity.

TABLE 3

|  | Number of bacteria | | Antibacterial |
| --- | --- | --- | --- |
|  | Inoculation | After 24 hours | activity level |
| Blank | $2.7 \times 10^5$ | $3.0 \times 10^6$ | — |
| Comparative Example 3 |  | $2.4 \times 10^5$ | 1.1 |
| Example 2 |  | $<1.0 \times 10^1$ | 5.5 |

As clearly seen from Table 3, Example 2 exhibited superior antibacterial activity with an antibacterial activity level of 5.5.

The biological implant of Example 2 described above was further subjected to a test for dissolution of iodine over time. Specifically, a test specimen formed to have a length of 50 mm, a width of 50 mm, and a thickness of 3 mm was immersed in 200 ml of saline solution (solution temperature: 23° C.) and, after the immersion for a predetermined period (time), the amount of iodine contained in the solution was determined by ICP mass spectrometry. The result is shown in FIG. 5.

Figure 5:
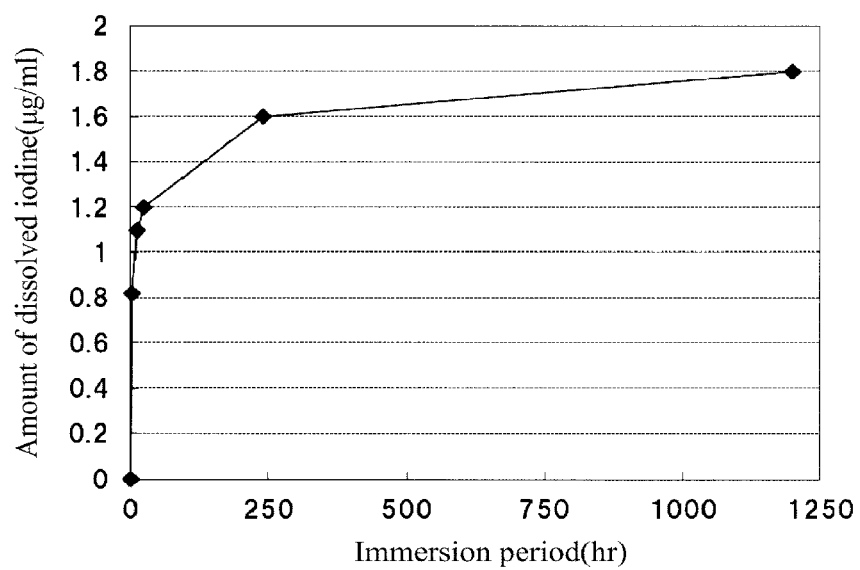
FIG. 5 is a graph showing the result of a test for dissolution of iodine over time in Example 2.

As clearly seen from FIG. 5, the biological implant of Example 2 successfully allowed iodine serving as an antibacterial substance to dissolve out over a long period of time. This result has demonstrated that the biological implant of Example 2 has superior performance in sustained-release of iodine and can exhibit antibacterial activity stably over a long period of time.

REFERENCE SIGNS LIST

1 Antibacterial biological implant
2 Substrate
3 Anodized coating
31 Iodine-rich layer
32 Portion other than iodine-rich layer
33 Microscopic hole
34 Microscopic asperity
100 Anodized coating
S Interface

The invention claimed is:

1. An antibacterial biological implant comprising
a substrate comprising a metal material; and
an anodized coating provided on the substrate,
the anodized coating comprising an iodine-containing layer, wherein a portion of the anodized coating other than the iodine-containing layer is an iodine-free layer,
wherein the iodine-containing layer is interposed between the substrate and the iodine-free layer, and
wherein the iodinine-containing layer is in contact with the substrate,
wherein the antibacterial biological implant is made by the process comprising:
performing an anodizing treatment on the substrate comprising a metal material with an electrolyte solution comprising sulfur to form an anodized coating comprising sulfur,
performing an acid treatment by contacting the anodized coating comprising, sulfur with an acid to dissolve the sulfur,
performing a washing treatment, and
forming the iodine-containing layer by immersing the acid treated anodized coating in an electrolyte solution comprising iodine.

2. The antibacterial biological implant according to claim 1, wherein the metal material is titanium or a titanium alloy.

3. The antibacterial biological implant according to claim 1, wherein the iodine-containing layer comprises an inorganic compound containing at least iodine.

4. The antibacterial biological implant according to claim 1, wherein the iodine-containing layer comprises an inorganic compound containing at least iodine and an element derived from the substrate.

5. The antibacterial biological implant according to claim 1, wherein an adhesive strength of the anodized coating to the substrate, as measured according to ASTNM F1147, is 22 MPa to 70 MPa.

6. The antibacterial biological implant according to claim 1, having an iodine content of 4 to 16 µg/cm$^2$.

7. The antibacterial biological implant according claim 1, having an iodine content of 10 to 16 µg/cm$^2$.

8. The antibacterial biological implant according to claim 1, capable of sustained-release of iodine.

9. The antibacterial biological implant according to claim 1, wherein the anodized coating has a thickness of 3 to 10 µm.

10. The antibacterial biological implant according to claim 1, wherein the iodine-containing layer has a thickness of 0.1 to 2 µm.

11. The antibacterial biological implant according to claim 1, wherein the metal material is titanium or a titanium alloy, and the iodine-containing layer comprises an inorganic compound containing at least iodine.

12. The antibacterial biological implant according to claim 1, having an iodine content of 4 µg/cm$^2$ to 25 µg/cm$^2$.

* * * * *